(12) United States Patent
Epstein (10) Patent No.: US 11,293,046 B2
(45) Date of Patent: Apr. 5, 2022

(54) METHOD AND DEVICE FOR CULTIVATION AND ANALYSIS OF NOVEL MICROBIAL SPECIES WITH UNKNOWN GROWTH REQUIREMENTS

(71) Applicant: Northeastern University, Boston, MA (US)

(72) Inventor: Slava Epstein, Dedham, MA (US)

(73) Assignee: Northeastern University, Boston, MA (US)

( * ) Notice: Subject to any disclaimer, the term of this patent is extended or adjusted under 35 U.S.C. 154(b) by 569 days.

(21) Appl. No.: 15/575,151

(22) PCT Filed: May 23, 2016

(86) PCT No.: PCT/US2016/033842
§ 371 (c)(1),
(2) Date: Nov. 17, 2017

(87) PCT Pub. No.: WO2016/187622
PCT Pub. Date: Nov. 24, 2016

(65) Prior Publication Data
US 2018/0155759 A1 Jun. 7, 2018

Related U.S. Application Data

(60) Provisional application No. 62/164,839, filed on May 21, 2015.

(51) Int. Cl.
*C12Q 1/24* (2006.01)
*C12M 1/26* (2006.01)
(Continued)

(52) U.S. Cl.
CPC ............... *C12Q 1/24* (2013.01); *C12M 23/02* (2013.01); *C12M 23/24* (2013.01); *C12M 29/00* (2013.01);
(Continued)

(58) Field of Classification Search
CPC ......... C12Q 1/24; C12M 23/02; C12M 23/24; C12M 33/14; C12M 41/36; C12M 41/48; C12M 29/00
See application file for complete search history.

(56) References Cited

U.S. PATENT DOCUMENTS 7,011,957 B2 3/2006 Lewis et al.
9,249,382 B2 2/2016 Gavrish et al.
(Continued)

FOREIGN PATENT DOCUMENTS

WO WO2013/148745 * 10/2014 ............ C12M 23/16

OTHER PUBLICATIONS

Ling, L. et al., "A new antibiotic kills pathogens without detectable resistance", Nature, 2015, 18 pgs., Macmillan Publishers Limited doi: 10.1038/nature14098.

*Primary Examiner* — Gautam Prakash
(74) *Attorney, Agent, or Firm* — Verrill Dana, LLP (57) ABSTRACT

The invention provides devices and methods for automatically preparing pure cultures of microbial cells under native environmental conditions. The devices and methods permit the discovery and investigation of novel microorganisms having unknown culture requirements from natural environments and microbiomes. Cultures obtained using the invention lead to the identification and isolation of novel biologically active compounds. The devices utilize a single entry pore in a thin membrane to select a single cell for clonal expansion.

17 Claims, 4 Drawing Sheets

(51) Int. Cl.
*C12M 1/36* (2006.01)
*C12M 1/00* (2006.01)
*C12M 1/04* (2006.01)
*C12M 1/34* (2006.01)

(52) U.S. Cl.
CPC ............ *C12M 33/14* (2013.01); *C12M 41/36* (2013.01); *C12M 41/48* (2013.01)

(56) References Cited

U.S. PATENT DOCUMENTS

| | | |
|---|---|---|
| 2004/0180334 A1 | 9/2004 | Halden |
| 2007/0243627 A1 | 10/2007 | Takayama et al. |
| 2007/0275451 A1* | 11/2007 | Gavrish et al. ........ C12M 23/20 435/243 |
| 2013/0093289 A1 | 4/2013 | Zhang |
| 2015/0167043 A1 | 6/2015 | Goluch et al. |

* cited by examiner

METHOD AND DEVICE FOR CULTIVATION AND ANALYSIS OF NOVEL MICROBIAL SPECIES WITH UNKNOWN GROWTH REQUIREMENTS

STATEMENT REGARDING FEDERALLY SPONSORED RESEARCH OR DEVELOPMENT

The invention was developed with financial support from Grant No. 1353853 from the National Science Foundation. The U.S. Government has certain rights in the invention.

BACKGROUND

Many microbial species found in natural environments do not survive and reproduce under standard laboratory culture conditions. As a result, most such species have not been studied or exploited, even though their existence is known from sequence analysis. Nevertheless, their genes, proteins, and metabolic products represent a rich repository of biological information and potential commercial products, including antibiotics, enzymes, and pharmaceuticals. There is a need for methods for culturing previously unknown microbes, especially bacteria found in natural environments.

Figure 1:
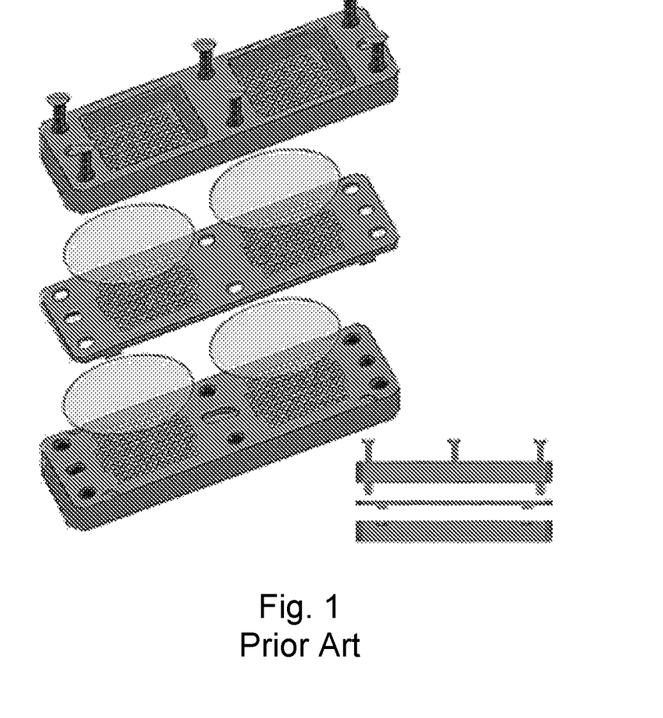
FIG. 1 shows a schematic representation of a prior art "iChip" device.

Devices have been developed for isolating and growing bacteria using the conditions of their native environment. For example, the iChip device described in U.S. Pat. No. 7,011,957, entitled "Isolation and Cultivation of Microorganisms from Natural Environments and Drug Discovery Based Thereon", and U.S. Pat. No. 9,249,382, entitled "Devices and Method for the Selective Isolation of Microorganisms" has led to the discovery of an important new antibiotic (see Ling, L., et al., Nature 517, 455-459 (2015). An iChip device is depicted in FIG. 1. It functions by placing microbial cells from an environment into agar-filled wells in the central plate, and sandwiching the wells between microporous membranes. The microporous membranes provide contact with the chemistry of the native environment when the assembled device is placed back into the environment from which the cells were obtained.

An approach to isolate bacteria from natural environments involving microfluidics is described in US Appl. No. 2015/0167043, entitled "Nanofluidic Device for Isolating, Growing, and Characterizing Microbial Cells". The device involves a combination of nanofluidic channels and microfluidic channels, and its fabrication is complex.

Thus, there remains a need for a simple, inexpensive device that can be deployed in large numbers in natural environments and can effectively yield pure cultures of bacteria and other microorganisms without human intervention.

SUMMARY OF THE INVENTION

The invention provides devices and methods for automatically preparing pure cultures of microbial cells having unknown culture requirements. The devices and methods permit the fully autonomous discovery and investigation of novel microorganisms from natural environments and microbiomes, without the need for an onsite operator. Whole networks of the devices can be placed and operated remotely, rendering them useful for isolated or hostile environments, including extraterrestrial environments. Cultures obtained using the invention can lead to the identification and isolation of novel biologically active compounds.

A key aspect of the invention is the use of a device having a single entry pore that is precisely fabricated in a membrane and has a suitable diameter and length to enable entry of only a single microbial cell into a growth chamber. Once the device is exposed to a medium containing microbial cells, a single cell will block the opening, and its progeny will grow into the growth chamber, forming a homogeneous culture. This is in contrast to the use of multiple pores per device, which results in a mixed culture that has limited utility for analyzing new species or strains and their capabilities. The device also features smaller feeding pores that allow the entry of chemicals from the original environment of the microorganism to support its survival and growth without the need to investigate or understand its growth requirements.

One aspect of the invention is a device for obtaining a monoculture of a microorganism from an environment. The device possesses a single microbial cell entry pore disposed in a membrane. The entry pore has a diameter in the range from about 200 nm to about 2000 nm and a pore length from about 1 $\mu$m to about 10 $\mu$m. The entry pore is exposed at a surface of the device disposed for contacting the environment. The device also possesses a plurality of feeding pores disposed in a membrane. Each feeding pore has a diameter smaller than the entry pore, so that microbial cells cannot enter or leave the growth chamber through the feeding pores, but chemicals from the environment can enter the growth chamber, and waste products can leave the growth chamber. The feeding pores are disposed for contacting a fluid containing molecular components from the environment. The device also includes a growth chamber for growing the microorganism that enters through the entry pore. The growth chamber is configured for containing a culture medium which is fluidically coupled to the entry pore and feeding pores.

The device may further contain a pump, an inlet port, and an outlet port, which are configured for the pump to collect environmental fluid from the inlet port, transport it into the device, and out through the outlet port. The environmental fluid can be pumped through the growth chamber or past the feeding pores. This is an important advantage over prior devices that rely on diffusion to deliver environmental nutrients and chemical agents. The use of a pump can provide a more reliable delivery and maintenance of environmental conditions than can diffusion. A pump, together with a reservoir containing water, liquid culture medium, or nutrients, allows the device to be used even in arid environments, such as deserts or environments found on Mars. In such cases, water or culture fluid can first be ejected into the nearby environment to the device in order to stimulate dormant microorganisms, which can then find their way into the growth chamber and produce a colony.

The device also can contain one or more fluid reservoirs and valves, which are used to add chemical agents to the growth chamber, so as to optimize growth of the microorganism. In various embodiments, the device also can include a processor for controlling pumps and valves and for receiving signals from sensors, as well as for carrying out a programmed set of instructions. Embodiments also can include a memory, a transmitter, a receiver, and a display. In certain embodiments, an array of growth chambers is present in the device, and the growth chambers may share common processor, pump(s), valve(s), fluid reservoir(s), transceiver, and display.

Another aspect of the invention is a method of producing a monoculture of a microorganism present in an environment. The method includes the steps of: (a) placing the device described above into an environment suspected of containing microorganisms; (b) allowing the device to collect and grow microorganisms; and (c) harvesting a monoculture of microorganisms from the device. The environment can be a natural outdoor environment, such as a body of water, sediment, soil, sand, rock, or other part of an ecosystem, either terrestrial or extraterrestrial, or an environment related to human activity, such as a food or food product or beverage, a fermentation, a chemical product, a consumer good, a sewage treatment facility, or a surface in a public area suspected of contamination or harboring a pathogen. The environment also can be a part of the microbiome of a human or other animal, such as a site of infection, the intestinal flora or feces, or a part of a plant. In embodiments the method includes remotely monitoring data from the device and/or controlling a function of the device using a computer or cell phone that communicates with a transceiver in the device and operates software on the device.

Still another aspect of the invention is a monoculture of microorganisms obtained using the method described above. The culture can be of a known or an unknown species or strain.

The invention can be further summarized by the following listing of embodiments.

1. A device for obtaining a monoculture of a microorganism from an environment, the device comprising:

a single entry pore disposed in a membrane, the entry pore having a diameter in the range from about 200 nm to about 2000 nm and a pore length from about 1 µm to about 10 µm, the entry pore exposed at a surface of the device disposed for contacting said environment;

a plurality of feeding pores disposed in a membrane, each feeding pore having a diameter smaller than the entry pore, the feeding pores disposed for contacting a fluid comprising molecular components from said environment; and a growth chamber for said microorganism, the growth chamber configured for containing a culture medium fluidically coupled to the entry pore and feeding pores.

2. The device of embodiment 1, wherein the entry pore is produced using an ion gun.

3. The device of embodiment 1 or embodiment 2. wherein the entry pore has an aspect ratio (length:diameter) of from about 5 to about 10.

4. The device of any of embodiments 1-3, wherein the entry pore and feeding pores are present in a single membrane.

5. The device of any of embodiments 1-3, wherein the entry pore and feeding pores are present in two different membranes.

6. The device of embodiment 5, wherein the two different membranes are disposed at two opposite facing sides of the device.

7. The device of any of embodiments 1-6, wherein the growth chamber comprises a growth medium for the microorganism.

8. The device of any of embodiments 1-7, wherein the feeding pores are disposed at a surface of the device contacting said environment.

9. The device of any of embodiments 1-8, further comprising one or more sensors.

10. The device of any of embodiments 1-9, further comprising a pump, an inlet port, and an outlet port, wherein device is configured so that the pump collects environmental fluid from the inlet port and transports it into the device and out through the outlet port.

11. The device of embodiment 10, wherein the device is configured so that said environmental fluid can be pumped into the growth chamber.

12. The device of embodiment 10, wherein the device is configured so that said environmental fluid can flow through the feeding pores into the growth chamber.

13. The device of any of embodiments 1-12, further comprising one or more fluid reservoirs and optionally one or more valves, the reservoirs and optional valves configured for adding one or more chemical agents to the growth chamber.

14. The device of embodiment 13, further comprising in said one or more reservoirs one or more chemical agents selected from the group consisting of nutrients, growth factors, amino acids, sugars, carbohydrates, lipids, electrolytes, proteins, peptides, antibodies, nucleic acids, mutagens, DNA alkylating agents, and DNA methylating agents.

15. The device of any of embodiments 9-15, further comprising a processor for controlling said pumps and valves to regulate flows of fluid within the device and to receive signals from said sensors according to a programmed set of instructions.

16. The device of embodiment 15, further comprising one or more of a memory for storage of data and instructions, a transmitter for sending data to a remote receiver, a receiver for receiving instructions for said processor, and a display.

17. A device comprising a plurality of devices of any of embodiments 1-16.

18. The device of embodiment 17 further comprising a plurality of pumps, fluid reservoirs, and sensors that are controlled and/or monitored by a single processor.

19. A method of producing a monoculture of a microorganism from an environment, the method comprising the steps of:

(a) placing the device of any of the preceding embodiments into an environment suspected of comprising microorganisms;

(b) allowing the device to collect and grow microorganisms in said growth chamber(s); and (c) harvesting one or more monocultures of microorganisms from said growth chamber(s).

20. The method of embodiment 19, wherein the device is a device of embodiment 16 or embodiment 18, the method further comprising monitoring data from the device and/or controlling a function of the device using a computer or cell phone.

BRIEF DESCRIPTION OF THE DRAWINGS

In FIG. 2A, the device has been placed in a soil environment. FIG. 2B shows that a bacterial cell has entered the entry pore and proliferated within the growth chamber. FIG. 2C shows an embodiment of the device with nanosensors in the growth chamber. In FIG. 2D, the user has transmitted instructions to operate the device.

DETAILED DESCRIPTION OF THE INVENTION

Devices according to the invention allow for automatic separation of microbial mixes into pure cultures of individual strains, making it possible to cultivate microorganisms in the form of pure cultures without manipulating their cells and in some embodiments without relying on diffusion of chemicals from the environment to support microbial growth. The devices can be fitted with reservoirs containing chemical compounds of choice and relevant nanosensors, The devices allow for experimentation with microorganisms targeted for cultivation, so as to learn their properties during growth in their natural environment. Further, cultures obtained using the device make possible the isolation of novel biologically active compounds from newly isolated species with commercial applications.

Figure 2A:
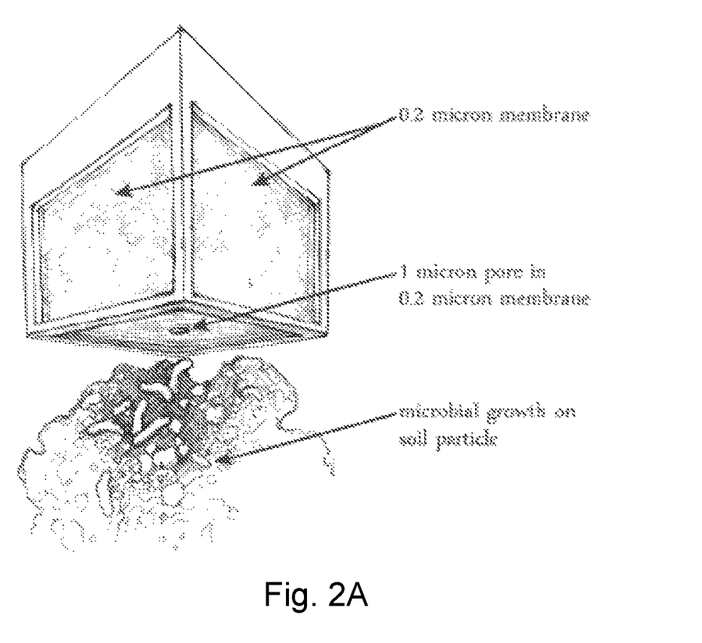
FIGS. 2A-2D show schematic illustrations of a device of the present invention in various stages of use.
Figure 2B:
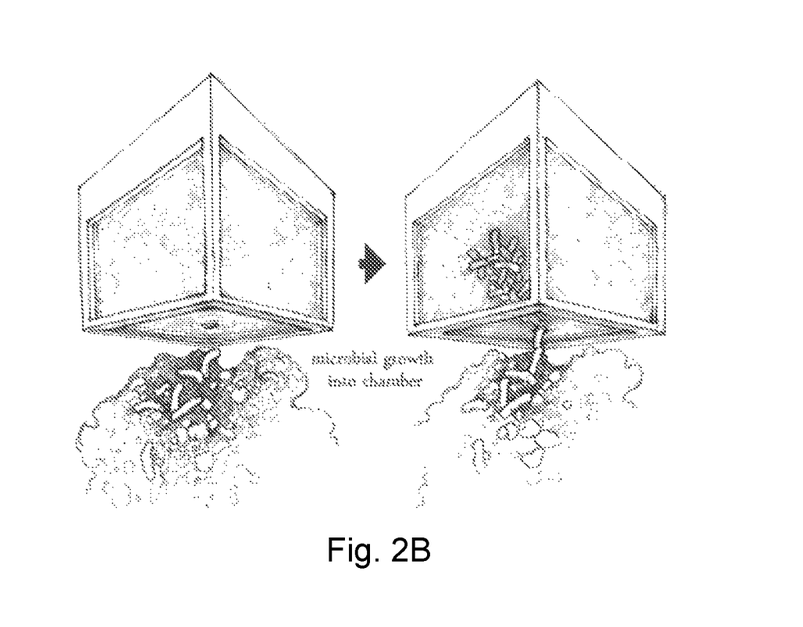
Figure 2C:
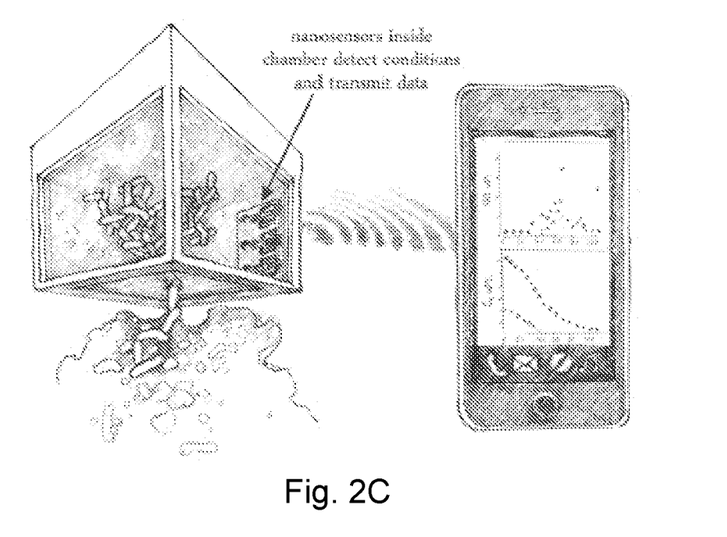
Figure 2D:
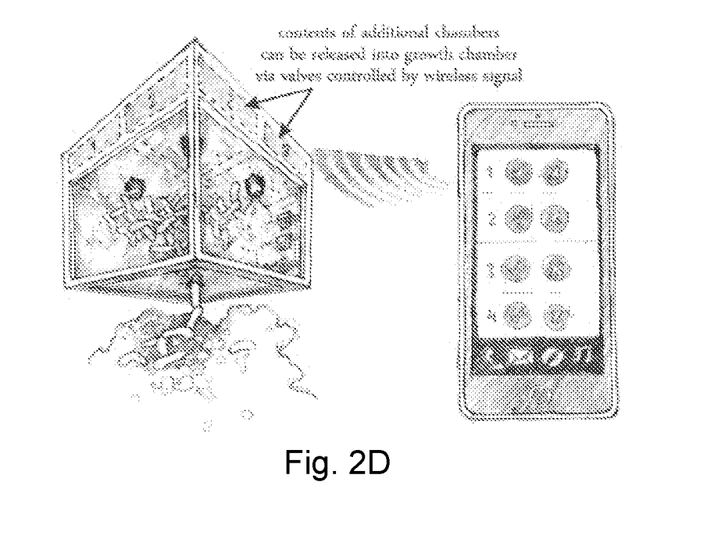

FIGS. 2A-2D illustrate the use of an embodiment of the device. In FIG. 2A, the device has been placed in a soil environment, and soil bacteria are present in the vicinity of the entry pore. Several walls of the device are semi-permeable membranes which allow solutes, nutrients, and metabolic waste products to enter and leave the growth chamber from the environment. FIG. 2B shows how a bacterial cell has entered through the single entry pore and has begun to proliferate within the growth chamber of the device. The time allowed for this growth to occur depends on the growth rate of the microorganism in the environment. FIG. 2C shows that nanosensors within the growth chamber sense the microbial growth and transmit data related thereto to a remote application running on a user's cell phone. Nanosensors can be nanoelectronic devices that measure physical parameters, such as light, temperature, pH, ionic strength, oxygen concentration, and the like, or can be functionalized with biomolecules such as antibodies, enzymes, nucleic acid aptamers, or other molecules that react to the presence of microbial cells, their molecular components, or their metabolites. Data obtained by the nanosensors can be transmitted to a remote monitoring device, such as a cell phone or computer. In FIG. 2D, the user has transmitted instructions to the device to release desired chemical agents into the growth chamber in order to test their effect on growth or other properties of the microbial culture, such as metabolic products, oxygen or carbon dioxide concentration, or pH.

The principal element of the device is a growth chamber connected to the outside environment by way of a single opening with a diameter similar to the dimensions of a single microbial cell, such as from about 200 nm to about 2000 nm, or from about 500 nm to about 1500 nm, or from 100, 200, 300, 400, 500, or 600 nm to about 800, 1000, 1200, 1500, 1700, or 2000 nm. Once the chamber is exposed to a medium containing microbial cells, be it a natural environment or a laboratory microbial culture or a mixture thereof, a single cell will block the opening and thus block subsequent passage of other cells to the growth chamber. If the growth chamber contains nutrients sufficient for growth of the entering cell or its progeny, growth will continue until the chamber is filled with the progeny of the entering cell, resulting in a monoclonal culture, genetically identical or essentially identical to the entering cell. The volume of the growth chamber can be selected according to the yield of cultured cells expected or desired, as well as according to the size limitations of the device and the number of chambers present on a single device. The sides or diameter of the growth chamber can be, for example, 100, 200, 300, 400, 500, 600, 700, 800, 900, 1000, 1200, 1500 µm, or 2000 µm in length.

A key aspect of the invention is the precision with which the opening (or "entry pore") is made. Suitable technologies include, but are not limited to, the use of an ion gun (i.e., a collimated ion beam), electron beam, or laser. The properties of the pore are critical to the success of the method. The pore should have a diameter similar to or slightly smaller than one of the dimensions of the cell type it is intended to trap. For example, a rod-shaped bacterium having dimensions of about 1.0×2.0 microns requires the entry pore to be about 1 micron in diameter. A circular pore cross-section is preferred as a good approximation of cellular profiles. Pore length should be sufficient for the first penetrating cell to become lodged within the pore, yet not so long as to inhibit progeny of the cell from entering the growth chamber. An aspect ratio (length to diameter) of from about 5 to about 10 is preferred. The pore is preferably straight along its length and cylindrical in shape. The membrane can be made of a hydrophilic biocompatible material. Polycarbonate is a preferred material. Also important is that the device contain one and only one entry pore coupled to each growth chamber; this assures that the microbial growth within the chamber represents a single clone.

Figure 3A:
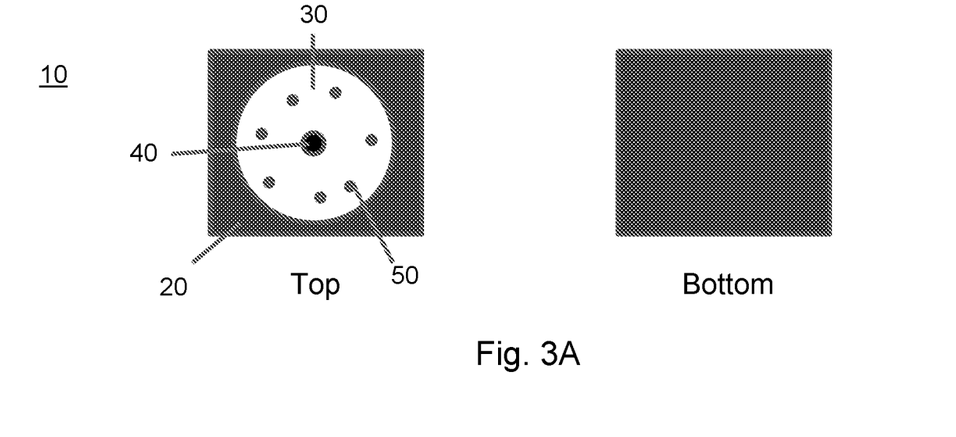
FIG. 3A shows a schematic illustration of a device having a single membrane that provides both entry pore and feeding pores.
Figure 3B:
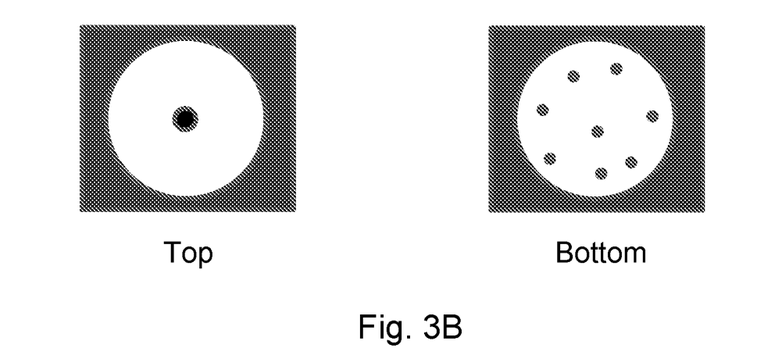
FIG. 3B shows a similar device, but having two membranes, one containing the entry pore and the other containing feeding pores.
Figure 3C:
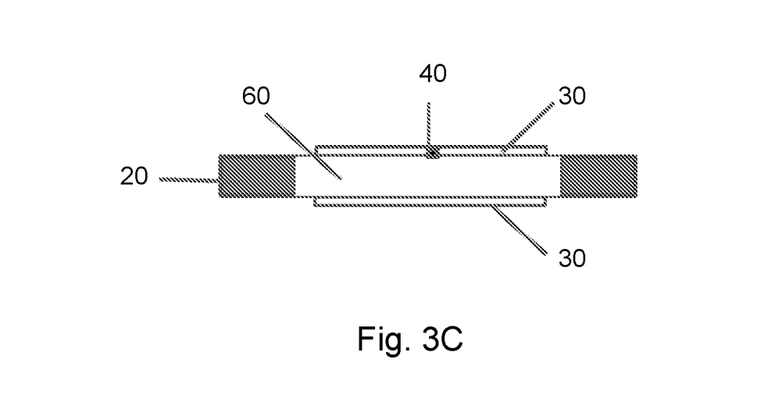
FIG. 3C shows a cross-section of the device of FIG. 3A or 3B.

FIGS. 3A-3C illustrate another embodiment of the device having one or two membranes disposed on opposite sides of a substrate comprising a chamber. In FIG. 3A, device 10 is formed of substrate 20, covered on a top side only by membrane 30, having entry pore 40 and a plurality of feed pores 50. In this embodiment, the bottom and sides of the growth chamber are solid, and only the top side communicates with the environment. FIG. 3B shows a related embodiment, but one that has entry pore on one side of the device and feed pores on the other side of the device. FIG. 3C shows a cross section of device 10, having substrate 20 containing growth chamber 60, which is covered on the top and bottom sides by membranes 30, one of which contains the single entry pore 40. Feed pores (not shown) can be disposed in either or both membranes. The membranes can be nanoporous polycarbonate filters, one of which has been modified to contain the entry pore. For example, the entry pore can be created in one nanoporous membrane using an ion gun.

The invention also provides methods of using the device to obtain monocultures of microbial cells found in an environment. In one such method, the device is immersed into an environment containing a mixed culture of several microbial species. The growth chamber is filled with a medium sufficient for the growth of these species. After a period of growth, each chamber contains a population of cells that started from a single cell. These populations can be collected from the device, and collectively represent all the species present in the sampled environment, in substantially the same proportion in which they occur in the environment. This provides for automatic separation of microbial mixes into monospecific cultures, with no participation of a researcher except to set up the device and harvest the cultures.

One or more sides of the chamber, or a portion thereof, can be made porous to chemical factors contained in the probed environment. The porous wall or membrane contains pores ("feeding pores") that are too small for microbes to penetrate (e.g, the pores are less than 200 nm, less than 150 nm, or less than 100 nm in diameter) but large enough for diffusion of molecules to occur (e.g., greater than 1 nm, 2 nm, 3 nm, 4 nm, 5 nm, 6 nm, 7 nm, 8 nm, 9 nm, 10 nm, 12 nm, 15 nm, 20 nm, 25 nm, 30 nm, 40 nm, or 50 nm). In this embodiment, no preloading of the chamber with nutrients is necessary, since nutrients will diffuse into the chamber. Similarly, no removal of waste products is required, since waste products will diffuse out of the chamber. If the device is deployed into a natural environment, the naturally occurring growth factors (i.e., nutrients and other chemicals needed for growth) present in that environment will diffuse in, recreating the growth conditions of the environment inside the chamber. This enables the growth of microbial species whose growth requirements are initially unknown. All that is necessary for cultivation is that the device be placed in physical contact with the environment containing microbial cells, such that the entry pore and feeding pores contact an aqueous or moist phase of the environment. Since no researcher is required to provide such contact, the device can be used in essentially any habitat on the planet, including extreme, hostile, or inaccessible environments, such as under an ice sheet in polar regions, in deep ocean trenches, or on extraterrestrial bodies. The device can even be transported to the target environment by an autonomous vehicle, moored within a body of water, or simply dropped to the bottom of a pond, lake, or the ocean, In another embodiment, the outside face of the membrane containing feeding pores is accessible to fluid from a fluid moving device or pump, such as a commercially available piezo-actuated membrane pump. The fluid moving device can slowly pump the liquid phase from the environment either past the porous membrane (containing either the entry pore, the feeding pores, or both) or directly through the growth chamber itself. This can provide the cells inside the growth chamber with naturally occurring nutrients and growth factors faster and more dependably than reliance on diffusion, and also can remove growth-inhibiting metabolites produced by the microbial culture inside the chamber.

In yet another embodiment, the device contains multiple growth chambers, e.g., arranged in an array, and each growth chamber can be connected to one or more reservoirs filled with specific chemical compounds or mixtures thereof. A valve can separate each growth chamber from the various reservoirs. By opening and closing such valves, the contents of the reservoir can be made available to the cells in the chamber, and their effect on microbial growth can be monitored, for example, through nanosensors built into the device. In a method of using such a device, a plurality of individual cells can each enter different entry pores and independently colonize different growth chambers. Such a device can be used in different ways. In one embodiment of using such a device, the device contains an array of growth chambers, and each chamber is initially filled with the same culture medium, or the environmental fluid is modified in the same manner. In another embodiment, the initial culture medium and/or the chemical additives vary across the array of the device. In this manner, more conditions can be tried out for a given cell type at one time, and the time to discovery of an appropriate culture medium and culture conditions can be shortened dramatically. An array device also can be employed so as to simultaneously obtain monocultures of a large number of species or strains at the same environmental location.

A number of optional components can be part of the device. An optical window allows monitoring cell condition, growth, and/or number, so as to detect signs of colony formation. Further optional components include a memory connected to the processor and/or sensors for data storage, a wireless transmitter to communicate data from the device to a remote monitoring station or user's cell phone or computer and receiver for receiving user instructions or modified programming, and a display to provide a readout of data or conditions of the device or within a growth chamber or reservoir of the device. In certain embodiments, the device includes an array of growth chambers, such as 2, 4, 10, 100, 1000, 10000, or 1000000 or more chambers on a single device, or can use a microtiter plate format, such as 6, 24, 96, 384, 1536, 3456, or 9600 wells on a single device.

This application claims the priority of U.S. Provisional Application No. 62/164,839 filed 21 May 2015 and entitled "Method and Device for Cultivation and Studying Novel Species with Unknown Growth Requirements", the whole of which is hereby incorporated by reference. The following US patents or printed publications are also incorporated by reference in their entireties: US Appl. No. 2015/0167043, U.S. Pat. Nos. 7,011,957, and 9,249,832.

As used herein, "consisting essentially of" allows the inclusion of materials or steps that do not materially affect the basic and novel characteristics of the claim. Any recitation herein of the term "comprising", particularly in a description of components of a composition or in a description of elements of a device, can be exchanged with "consisting essentially of" or "consisting of".

While the present invention has been described in conjunction with certain preferred embodiments, one of ordinary skill, after reading the foregoing specification, will be able to effect various changes, substitutions of equivalents, and other alterations to the compositions and methods set forth herein.

What is claimed is:

1. A device for obtaining a monoculture of microbial cells from an environment, the device comprising:
    a first membrane comprising only a single entry pore for microbial cells, the entry pore having a diameter in the range from about 200 nm to about 2000 nm and a pore length from about 1 μm to about 10 μm, wherein the entry pore is produced using an ion gun, an electron beam, or a laser, and wherein the entry pore is exposed at a surface of the device disposed for contacting said microbial cells in said environment;
    one or more second membranes, each second membrane comprising a plurality of feeding pores, each feeding pore having a diameter smaller than the entry pore, the feeding pores disposed for contacting a fluid comprising molecular components from said environment; and
    a growth chamber for said microbial cells, the growth chamber configured for containing a culture medium fluidically coupled to the entry pore and feeding pores.

2. The device of claim 1, wherein the entry pore has an aspect ratio (length:diameter) of from about 5 to about 10.

3. The device of claim 1, wherein the first membrane and one second membrane are disposed at the two opposite facing sides of the device.

4. The device of claim 1, wherein the growth chamber comprises a growth medium for the microorganism.

5. The device of claim 1, wherein the feeding pores are disposed at a surface of the device contacting said environment.

6. The device of claim 1, further comprising one or more sensors.

7. The device of claim 1, further comprising a pump, an inlet port, and an outlet port, wherein the device is configured so that the pump collects environmental fluid from the inlet port and transports it into the device and out through the outlet port.

8. The device of claim 7, wherein the device is configured so that said environmental fluid can be pumped into the growth chamber.

9. The device of claim 7, wherein the device is configured so that said environmental fluid can flow through the feeding pores into the growth chamber.

10. The device of claim 1, further comprising one or more fluid reservoirs and optionally one or more valves, the reservoirs and optional valves configured for adding one or more chemical agents to the growth chamber.

11. The device of claim 10, further comprising in said one or more reservoirs one or more chemical agents selected from the group consisting of nutrients, growth factors, amino acids, sugars, carbohydrates, lipids, electrolytes, proteins, peptides, antibodies, nucleic acids, mutagens, DNA alkylating agents, and DNA methylating agents.

12. The device of claim 7, further comprising one or more sensors and a processor for controlling said pumps and valves to regulate flows of fluid within the device and to receive signals from said sensors according to a programmed set of instructions.

13. The device of claim 12, further comprising one or more of a memory for storage of data and instructions, a transmitter for sending data to a remote receiver, a receiver for receiving instructions for said processor, and a display.

14. A device comprising a plurality of devices of claim 1.

15. The device of claim 14 further comprising a plurality of pumps, fluid reservoirs, and sensors that are controlled and/or monitored by a single processor.

16. The device of claim 1, wherein one or more second membranes form one or more walls of the device.

17. The device of claim 16, wherein second membranes form four walls of the device.

\* \* \* \* \*